United States Patent
Snyder et al.

(10) Patent No.: US 6,232,609 B1
(45) Date of Patent: May 15, 2001

(54) GLUCOSE MONITORING APPARATUS AND METHOD USING LASER-INDUCED EMISSION SPECTROSCOPY

(75) Inventors: Wendy J. Snyder, Hermosa Beach; Warren S. Grundfest, Los Angeles, both of CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

(21) Appl. No.: 08/566,313

(22) Filed: Dec. 1, 1995

(51) Int. Cl.[7] .................................................. G01N 21/64
(52) U.S. Cl. ..................................... 250/461.1; 250/459.1
(58) Field of Search ............................ 250/461.1, 458.1, 250/459.1

(56) References Cited

U.S. PATENT DOCUMENTS

| | | | |
|---|---|---|---|
| 3,807,862 | | 4/1974 | Hatzenbuhler ........................ 356/75 |
| 4,031,398 | | 6/1977 | Callis et al. ...................... 250/458.1 |
| 4,678,277 | | 7/1987 | Delhaye et al. ..................... 356/301 |
| 4,957,366 | * | 9/1990 | Koshi et al. ...................... 250/458.1 |
| 5,037,200 | | 8/1991 | Kodama .............................. 356/252 |
| 5,212,099 | | 5/1993 | Marcus ............................... 436/172 |
| 5,243,983 | | 9/1993 | Tarr et al. .......................... 128/633 |
| 5,280,788 | | 1/1994 | Janes et al. ......................... 128/665 |
| 5,337,139 | * | 8/1994 | Shirasawa ........................ 250/461.1 |
| 5,341,805 | | 8/1994 | Stavridi et al. ..................... 128/633 |
| 5,348,018 | | 9/1994 | Alfano et al. ....................... 128/665 |
| 5,435,309 | * | 7/1995 | Thomas et al. ...................... 128/633 |
| 5,445,972 | * | 8/1995 | Tarcha et al. ....................... 436/544 |
| 5,446,681 | * | 8/1995 | Gethner et al. ..................... 364/554 |
| 5,491,344 | * | 2/1996 | Kenny et al. ..................... 250/461.1 |

FOREIGN PATENT DOCUMENTS

| | | |
|---|---|---|
| 0 589 191 A1 | 3/1994 | (EP) . |
| 0 623 307 A1 | 11/1994 | (EP) . |
| 0 631 137 A2 | 12/1994 | (EP) . |
| WO 93/01745 | 2/1993 | (WO) . |
| WO 94/16614 | 8/1994 | (WO) . |

OTHER PUBLICATIONS

Geladi, Paul, et al., "Partial Least–SquaresRegression: A Tutorial," Analytica Chimica Acta, Elsevier Science Publishers B.V., Amsterdam, (1986), pp. 1–17.

Bell, Alasdain F., "Vibrational Raman Optical Activity Study of D–glucose," CarbohydrateResearch, 1994, vol. 257, pp. 11–24.

* cited by examiner

Primary Examiner—Edward P. Westin
Assistant Examiner—Richard Hanig
(74) Attorney, Agent, or Firm—Pretty, Schroeder & Poplawski, P.C.

(57) ABSTRACT

A glucose monitor, and related method, determines the concentration of glucose in a sample with water, using a predictive regression model. The glucose monitor illuminates the sample with ultraviolet excitation light that induces the water and any glucose present in the sample to emit return light that includes raman scattered light and glucose emission or fluorescence light. The return light is monitored and processed using a predictive regression model to determine the concentration of glucose in the sample. The predictive regression model accounts for nonlinearities between the glucose concentration and intensity of return light within different wavelength bands at a predetermined excitation light energy or the intensity of return light within a predetermined wavelength band at different excitation energy levels. A fiber-optic waveguide is used to guide the excitation light from a laser excitation source to the sample and the return light from the sample to a sensor.

13 Claims, 9 Drawing Sheets

ACTUAL (O) AND PREDICTED CONCENTRATIONS BY PLS (+) FOR THE CALIBRATION DATA

THE EMISSION SPECTRA OF 500 mg/dl OF GLUCOSE IN WATER

GLUCOSE MONITORING APPARATUS AND METHOD USING LASER-INDUCED EMISSION SPECTROSCOPY

BACKGROUND OF THE INVENTION

This invention relates to glucose monitoring, and more particularly, to glucose level monitoring using laser-induced emission spectroscopy.

Millions of people, afflicted with diabetes, must periodically monitor their blood glucose level because their bodies are unable to maintain a constant blood glucose level without diet adjustments and periodic insulin injections. Most popular methods for monitoring blood glucose levels require a small blood sample that is periodically drawn from the body for analysis.

Recently, noninvasive optical techniques have been developed to monitor the blood's glucose level using infrared absorption through a portion of the body. However, infrared absorption techniques are susceptible to accuracy problems, in part because glucose has more than 20 infrared absorption peaks, many of which overlap with the absorption peaks of other constituents in the body.

Fluorescence spectroscopy using ultraviolet (UV) excitation light has been introduced for monitoring glucose levels. This technique requires, among other things, the monitoring of a spectral peak within the induced fluorescence spectrum. Accurately locating the peak may be difficult for a low-level fluorescence signal in the presence of noise. Increasing the intensity of the excitation light may not be a desirable option because of concerns of UV exposure to the body. Also, known fluorescence spectroscopic techniques generally fail to take full advantage of information contained in the fluorescence spectrum at wavelengths other than the peak wavelength and fail to account for certain nonlinear relationships between the glucose level and the resulting emission spectra.

From the discussion above, it should be apparent that there is a need for an apparatus, and related method, for monitoring glucose that is simple and rapid to use, and that provides good accuracy in spite of nonlinearities or low signal-to-noise levels. The present invention fulfills these needs.

SUMMARY OF THE INVENTION

The present invention is embodied in an apparatus, and related method, that determines the concentration of glucose in a sample that includes water, by directly monitoring induced glucose ultraviolet and visible (UV-visible) emission light from the sample. The apparatus compensates for nonlinearities between these parameters and the glucose.

The apparatus includes a light source, a sensor, and a processor. The light source emits ultraviolet excitation light of at least one predetermined energy level. The excitation light is directed at a sample to produce return light from the sample. The return light includes induced emissions of light produced as a result of interactions between the excitation light and any glucose with water present in the sample. The sensor monitors the return light and generates at least three electrical signals indicative of the intensity of return light associated with glucose concentration distinguishing characteristics of the emission light. The processor processes the electrical signals, using a predictive model, to determine the concentration of glucose in the sample. In one feature of the invention, the predictive model is defined using six latent variables. The latent variables are used to derive prediction coefficients that are associated with the glucose concentration distinguishing characteristics.

In a more detailed feature of the invention, the intensity of the excitation light remains relatively constant while the sensor generates the electrical signals. Further, the at least three electrical signals indicate the intensity of return light within a respective number of predetermined wavelength bands within the wavelength band of the emission light. In another feature, the sensor may includes a first detector adapted to detect the return light within a first wavelength band and generate a first electrical signal, a second detector adapted to detect the return light within a second wavelength band and generate a second electrical signal, and a third detector adapted to detect the return light within a third wavelength band and generate a third electrical signal.

In yet another more detailed feature of the invention, the sensor monitors the intensity of return light within eight different wavelength bands and generates eight electrical signals, each indicative of the intensity of return light within a respective wavelength band. More particularly, using an excitation light having a wavelength of about 308 nanometers, the eight wavelength bands may be centered at about 342, 344, 347, 352, 360, 370, 385 and 400 nanometers, respectively. Alternatively, the sensor may generate a plurality of electrical signals that indicate the intensity of return light substantially continuously across an extended wavelength spectrum associated with the emission light.

In another more detailed feature of the invention, the energy of the excitation light is varied over several predetermined energy levels, and the sensor generates, at each intensity level, a first electrical signal based on the intensity of return light within a wavelength of the emission light associated with raman scattering, and a second electrical signal based on the intensity of return light within a wavelength band of the emission light associated with a peak of a broad glucose emission band. Further, the apparatus may include one or more waveguides for transmitting the excitation light from the light source to the sample and for transmitting the return light from the sample to the sensor.

In a related method of the invention, a regression model is provided that accounts for a nonlinear relationship between the concentration of glucose in a sample and an electrical signal based on certain glucose concentration distinguishing characteristics of a light emission spectrum that includes UV-visible emission light produced by glucose related interactions with the excitation light. Further, a sample is caused to produce a light emission spectrum that includes emission light produced by any glucose related interaction or direct fluorescence, and a plurality of electrical signals are generated that represent the glucose concentration distinguishing characteristics. Finally, the plurality of electrical signals are processed, using the regression model, to determine the glucose concentration and an electrical signal generated based on the glucose concentration determined using the regression model.

Other features and advantages of the present invention should become apparent from the following description of the preferred embodiment, taken in conjunction with the accompanying drawings, which illustrate, by way of example, the principles of the invention.

DESCRIPTION OF THE PREFERRED EMBODIMENTS

As shown in the exemplary drawings, the present invention is embodied in a glucose monitoring system 10, and related method, for determining the concentration of glucose in a sample 12 by monitoring the glucose ultraviolet and visible (UV-visible) light emission spectra at several wavelengths or excitation intensities while compensating for the nonlinear relationship between the glucose concentration of these parameters. The system provides good accuracy in spite of the nonlinearities or low signal-to-noise levels.

Figure 1:
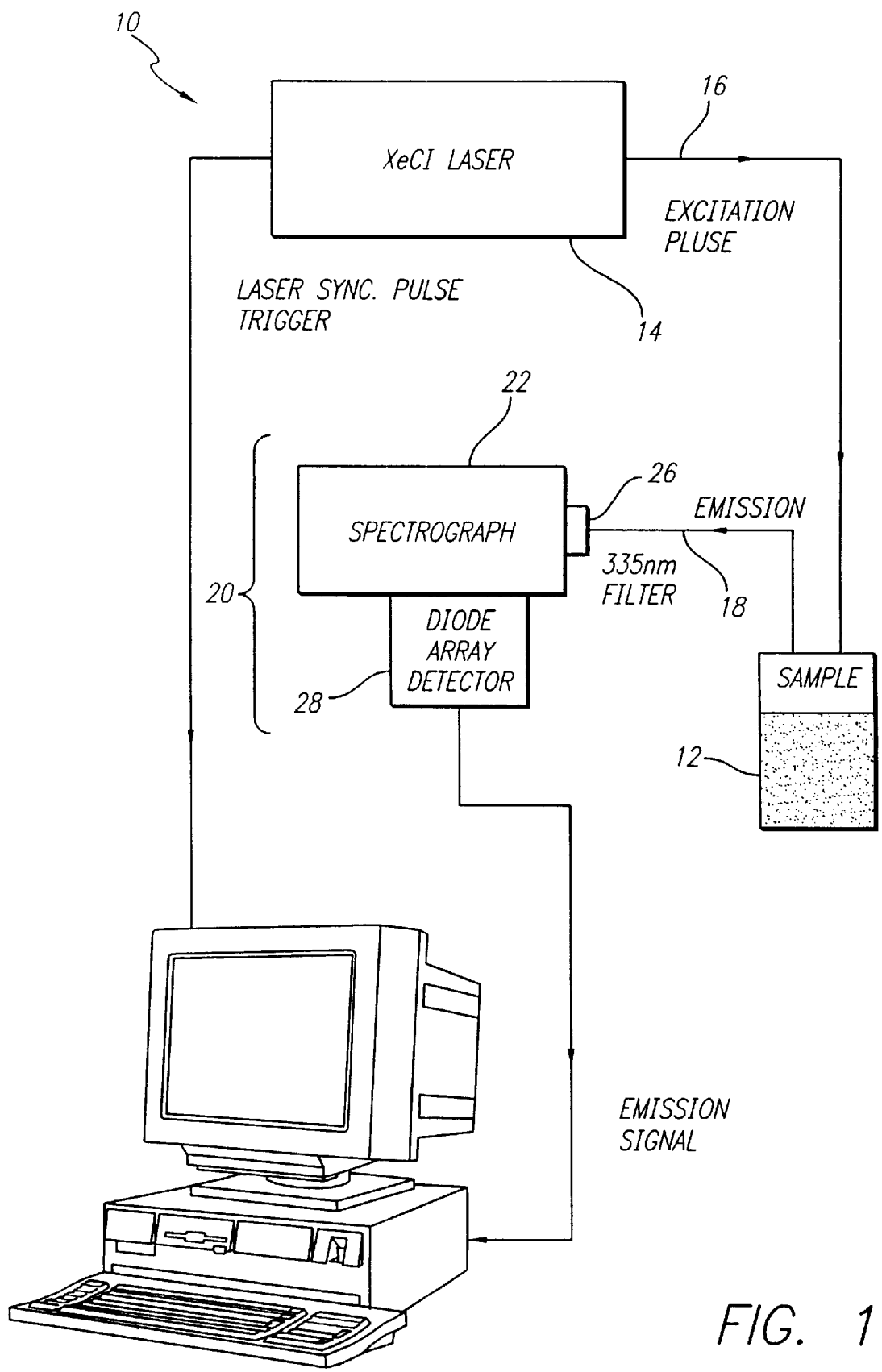
FIG. 1 is a block diagram of a glucose monitoring system embodying the invention.

In the glucose monitoring system 10 shown in FIG. 1, an excitation source 14 directs ultraviolet excitation light to the sample 12 through an optical fiber 16, to induce any glucose within the sample to absorb and reemit or to scatter the excitation light. An optical fiber or fiber bundle 18 collects return light emitted by the sample. The return light includes any glucose emissions induced by the excitation light. A sensor 20 monitors the return light within different wavelength bands of interest and generates a series of electrical signals based on the intensity of return light received in the wavelength band or bands of interest. In one embodiment, the sensor includes a spectrograph 22 which resolves the return light by separating the return light by wavelength. An analyzer 24 or processor, having a prediction model that associates the intensity of return light of interest with the concentration of glucose in the sample, processes the electrical signals generated by the sensor, compares the results with the model, and generates an electrical signal representing the concentration of glucose in the sample.

A useful excitation source 14 is an excimer laser producing light having a wavelength of about 308 nanometers, a full width half maximum (FWHM) pulse width of about 120 nanometers, and a repetition rate of about 5 hertz. It is believed that glucose more efficiently absorbs excitation light having a wavelength between 260 to 280 nanometers and it would be desirable to have an excitation wavelength in that range. However, as presently understood, excitation sources operating at these wavelengths generally are of limited availability. The excitation light can be provided by any type of generally narrow-band ultraviolet light source and generally can have a wavelength from about 250 to 350 nanometers.

The excitation light is guided to the sample 12 through a fused silica fiber 16 having a 600 micron core diameter. The excitation light's energy, emitted from the fiber, is set to predetermine levels from about 0.5 to 10 millijoules per pulse (0.54 to 36 millijoules per square millimeter per pulse). The induced emissions from the sample, or return light, preferably is collected using a bundle of six fused silica fibers 18, each fiber having a 300 micron core. The collection fibers guide the return light to the sensor 20.

The sensor 20 may include individual light-sensitive diodes, with appropriate bandpass filters, or as discussed above, may include a spectrograph 22 that resolves a broad spectrum of the return light. A spectrograph was used to collect the data discussed below. A long pass filter 26 (Schott WG335) is placed within the spectrograph to filter from the return light, any excitation light that may have been collected by the collection fibers 18. An ultraviolet enhanced grating (150 grooves per millimeter), located after an entrance slit of the spectrograph disperses the return light into its constituent wavelengths. A silicon diode array detector 28 having 1024 elements collects the dispersed return light and generates an electrical signal that serially represents the intensity of return light collected in each element. An EG&G optical multichannel analyzer (OMA III) receiving the electrical signal can display a graph representing the intensity of return light within the desired wavelength band or bands of interest.

Figure 2:
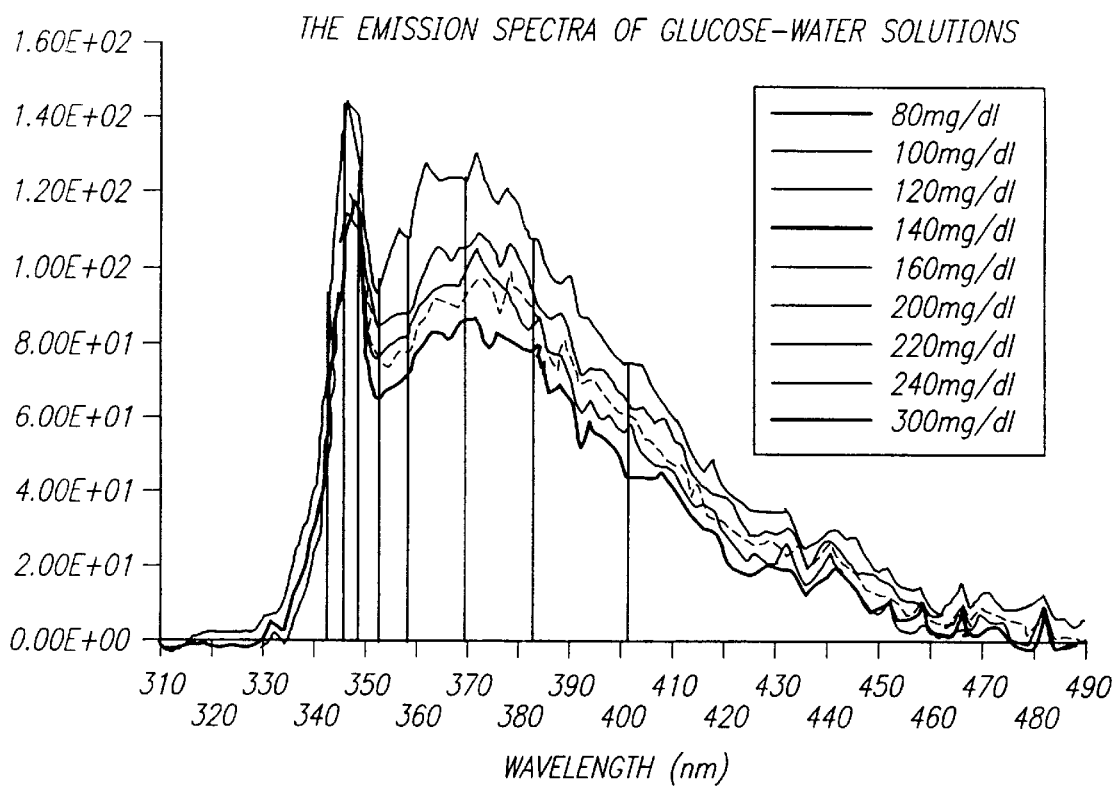
FIG. 2 is a graph of the intensity of glucose emission versus wavelength for different concentrations of glucose in water illuminated with laser excitation light having a wavelength of 308 nanometers.

Before the concentration of glucose can be determined in a sample having an unknown glucose concentration, a model must be prepared that accounts for certain nonlinearities between the glucose concentration and certain measured parameters. The process of deriving the model is better understood with reference to FIG. 2. The spectrum shown in FIG. 2 is the emission spectra of different glucose concentrations after excitation with an ultraviolet excimer laser light having a wavelength of 308 nanometers. Each spectrum is shown to have a double peak shape. One spectral peak is associated with a narrow wavelength band centered at about 346 nanometers, apparently produced as a result of vibrational raman scattering, and a broad emission band 28 centered at approximately 440 nanometers, believed to be produced largely by direct glucose and water fluorescence.

The wavelength of the peak associated with the narrow raman scattering band is approximately 30 to 50 nanometers longer than the wavelength of the excitation light and shifts generally in proportion to shifts in the wavelength of the excitation light. The shape and emission wavelengths of the broad glucose emission band generally is not a direct function of the excitation wavelength.

As shown in Table I below, the emission intensity associated with eight representative wavelengths does not vary linearly with glucose concentration over the clinically relevant range of 80 to 300 milligrams per deciliter. The eight representative wavelength are indicated by the vertical lines in the graph of FIG. 2.

TABLE I

| Concentr (mg/dl) | wavelength (nanometers) | | | | | | | |
|---|---|---|---|---|---|---|---|---|
| | 342 | 344 | 347 | 352 | 360 | 370 | 385 | 400 |
| 80 | 56.3 | 116 | 87.4 | 86.9 | 95.4 | 106 | 80.8 | 54.6 |
| 100 | 72.5 | 145 | 105 | 103 | 120 | 123 | 98.9 | 60.3 |
| 120 | 67.8 | 126 | 91.9 | 78.2 | 92.9 | 103 | 74.6 | 45.9 |
| 140 | 62.1 | 121 | 93.9 | 80.0 | 95.8 | 102 | 76.2 | 47.6 |
| 160 | 57.9 | 120 | 81.4 | 73.4 | 87.8 | 104 | 75.3 | 46 |
| 200 | 51.1 | 102 | 77.3 | 80.1 | 88.3 | 101 | 71.3 | 46.3 |
| 220 | 48.6 | 104 | 74.4 | 74.2 | 83.8 | 96.6 | 71.1 | 42.4 |
| 240 | 58.6 | 102 | 84.6 | 78.5 | 84.5 | 95.9 | 73.4 | 46.6 |
| 300 | 55.4 | 107 | 71.9 | 67.9 | 77.9 | 86.9 | 65.1 | 4.19 |

Figure 3:
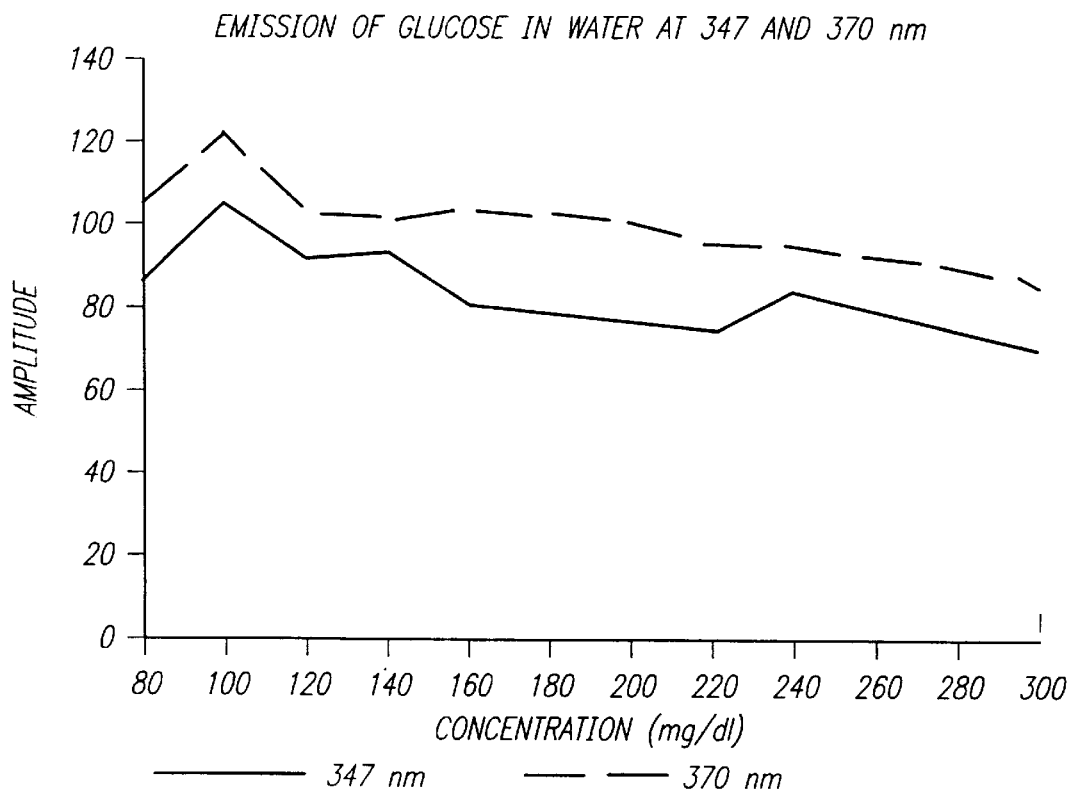
FIG. 3 is a graph of the intensity of glucose emission at two wavelengths verses glucose concentration in water, illuminated with laser excitation light having a wavelength of 308 nanometers and an excitation energy of 1 millijoule per pulse.

Instead, as shown in FIG. 3, the relationship between measured intensity and glucose concentration is highly nonlinear and presents a different profile at different wavelengths. More particularly, as the glucose concentration in water increases, the intensity at a wavelength of 370 nanometers generally increases as the glucose concentration increases until the concentration reaches about 100 milligrams per deciliter. At this point, the intensity then begins to taper off or decrease with increasing concentration. Similarly, the intensity at at a wavelength of 347 nanometers, generally the wavelength of the raman scattering peak generally increases and then decreases with increasing glucose concentration. Note however, that the rate of change for the intensity versus glucose concentration is different for each of the curves.

In designing a model to predict the glucose concentration, several approaches are available to account for the nonlinear effects discussed above. One method is to restrict the calibration curve to small segments which are approximated by a simple linear model. Another method is to perform a transformation on the nonlinear variable. Finally, the calibration curve can be modeled using a polynomial fit.

Polynomial curve fitting for providing a predictive model is achieved using statistical techniques based on a least squares regression method. A common regression technique known as partial least squares (PLS) regression has been found to provide a robust model in that the model parameters do not change significantly when new samples are taken. The algorithms and theoretical basis for PLS predictive modeling can be found in Brereton, R. G. *Chemometrics: Applications of Mathematics and Statistics to Laboratory Systems*, New York: Ellis Horwood, 1990. A basic overview of PLS regression can be found in Gerald and Kowalski, "Partial Least-Squares Regression: A Tutorial" *Analytical Chimica Acta* 185 (1986):1–17.

The PLS regression technique begins by "autoscaling" each variable such that all the variables are equally influential in the prediction. The PLS regression technique uses principle component analysis, also known as singular value decomposition or eigenvector analysis, to represent the dependent and independent matrices. In principle component analysis, a NIPALS algorithm is used to define a data matrix of independent variables. PLS regression techniques introduce a weighting factor into the regression model. The PLS algorithm gives a sequence of models, the best model being the one that minimizes the cross-validation.

Figure 4:
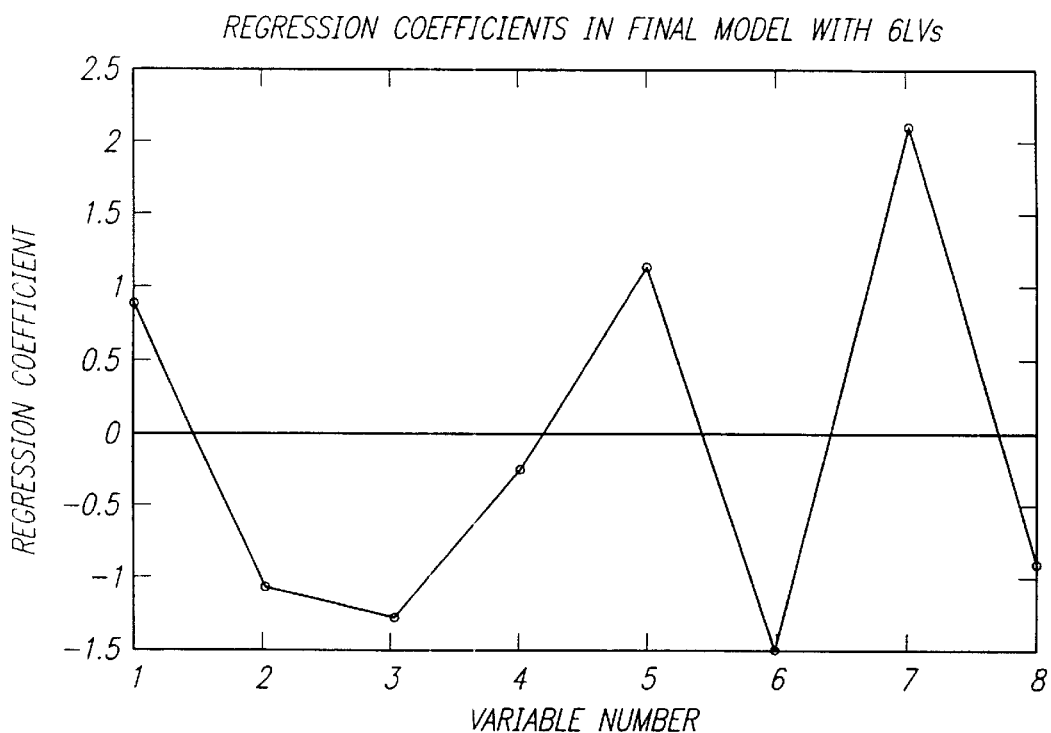
FIG. 4 is a graph of the regression coefficient verses the latent variable number, derived from a partial least square (PLS) analysis using the intensities at eight wavelength indicated in the graph of FIG. 2.

For example, from Table I, a data matrix of independent variables (the glucose concentration is the dependent variable), consisting of the emission intensity at the different: wavelengths, is provided to a data processing routine that performs the PLS regression. In this example, the data processing routine is included in the "PLS$_{13}$Toolbox Version 1.3" available from Barry M. Wise, 1415 Wright Avenue, Richland, Wash. 99352 (E-mail: bm$_{13}$wise@pnl.gov). The routines in the "Toolbox" are presently intended for use with the MATLAB™ software package available from The Mathworks, Inc., 24 Prime Park Way, Natick, Mass. 1760. In using the routine, the matrix associated with the spectral intensities at each wavelength and the matrix associated with the concentration values have their means removed before processing. The routine calculates a regression vector shown in FIG. 4 and in Table II below. The scalar components of the regression vector are the prediction coefficients for each wavelength.

TABLE II

| Number | Wavelength | Coefficient |
|---|---|---|
| 1 | 342 | 0.8946 |
| 2 | 344 | −1.0627 |
| 3 | 347 | −1.2613 |
| 4 | 352 | −0.2548 |
| 5 | 360 | 1.1316 |
| 6 | 370 | −1.4846 |
| 7 | 385 | 2.0911 |
| 8 | 400 | −0.9403 |

To make a prediction on a sample of unknown concentration, the intensity at each of the eight wavelengths is measured. These eight measured values are scaled and multiplied by the regression vector, i.e., the eight wavelength coefficients in Table II. The result is a scaled concentration prediction. The scaled predicted concentration must be rescaled to provide a concentration value in the original units.

Because eight different wavelengths were used, the model can yield up to eight latent variables. Table III below shows the percent of variance that was accounted for with the addition of each latent variable to the model.

TABLE III

Percent Variance Captured by PLS Model

| LV # | X-Block This LV | Total | Y-Block This LV | Total |
|---|---|---|---|---|
| 1 | 75.6695 | 75.6695 | 77.9674 | 77.9674 |
| 2 | 8.5652 | 84.2347 | 15.3105 | 93.2779 |
| 3 | 3.4081 | 87.6428 | 3.9910 | 97.7993 |
| 4 | 8.9551 | 96.5979 | 0.5305 | 97.7993 |
| 5 | 1.9529 | 98.5508 | 0.4636 | 98.2629 |
| 6 | 0.5536 | 99.1045 | 0.6821 | 98.9450 |
| 7 | 0.2573 | 99.3618 | 0.7112 | 99.6562 |
| 8 | 0.6382 | 100.00 | 0.0031 | 99.6593 |

In developing the predictive model, the cross-validation calculation is used to determine the optimum number of latent variables to use in the model. The cross-validation is performed by using one spectra chosen at random to test the model. The cross-validation is repeated ten times, randomly choosing a different spectra to test the model. The results of the cross-validation are shown in the press plot of FIG. 5 as a plot of the prediction residual sum of squares (PRESS) versus the number of latent variables used in the model. The PLS analysis yielded a model of six latent variables.

Figure 5:
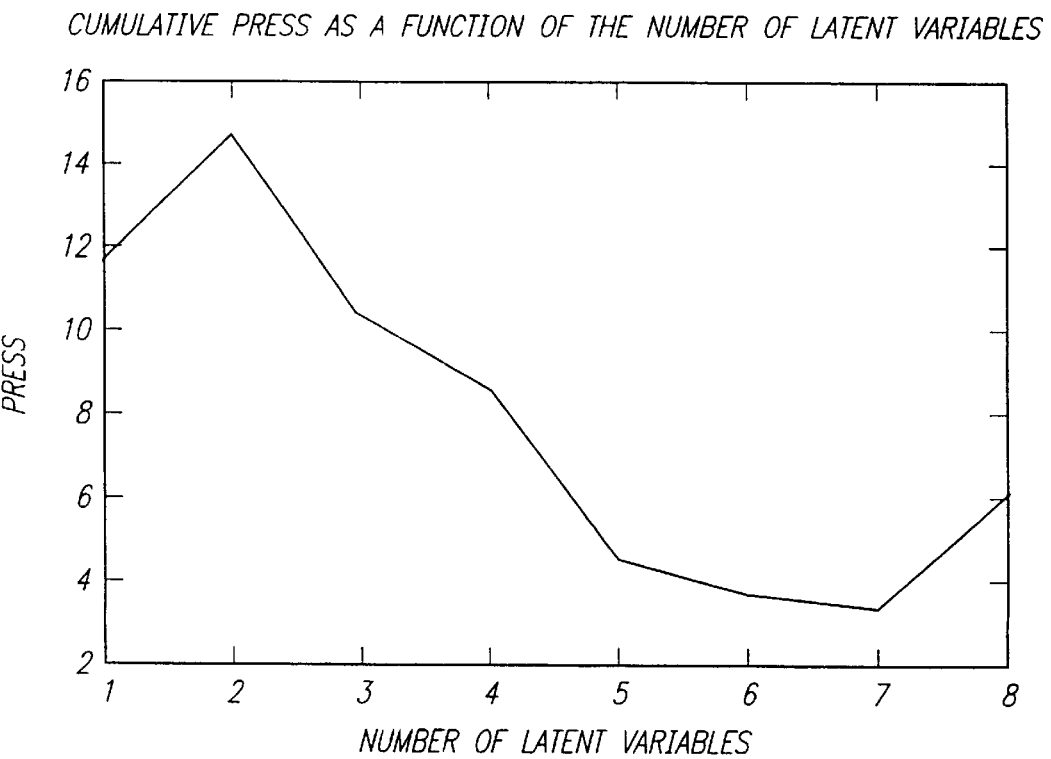
FIG. 5 is a graph of the prediction residual sum of squares (PRESS,) versus number of latent variables, using one spectra at a time to test the PLS model derived from intensities at the eight wavelengths indicated in the graph of FIG. 2.
Figure 6:
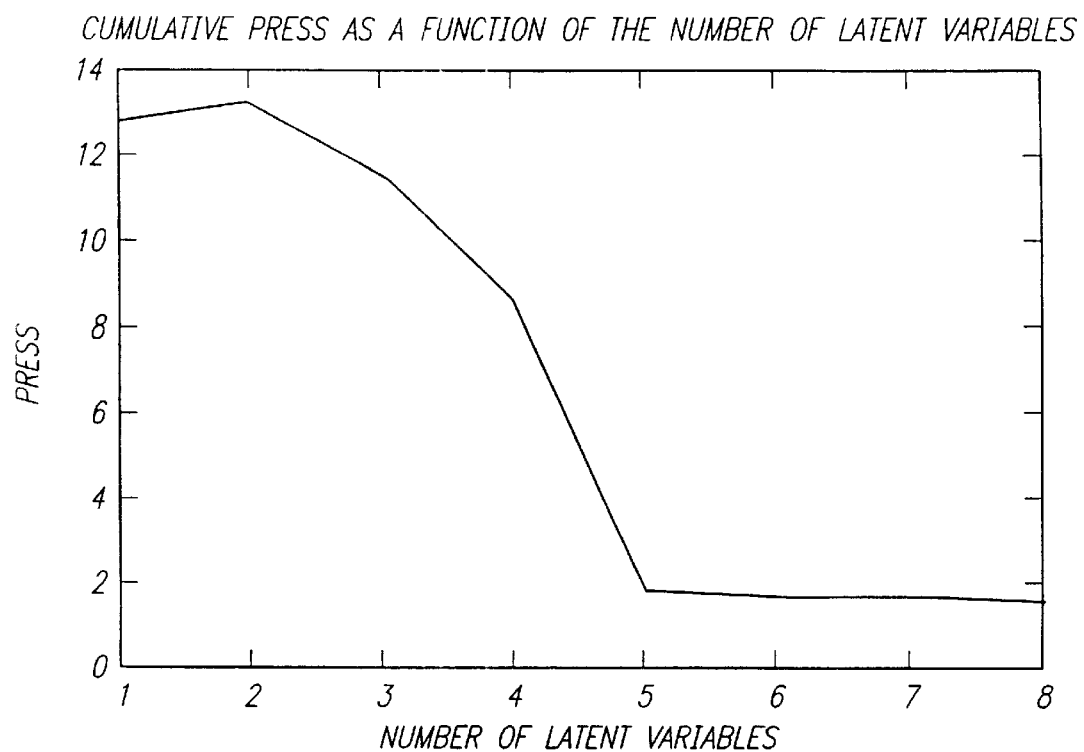
FIG. 6 is a graph of the PRESS versus number of latent variables using two spectra at a time to test the PLS model derived from intensities at the eight wavelengths indicated in the graph of FIG. 2.

The cross-validation was repeated using blocks of two spectra at a time to test the model. The press plot associated with the two spectra cross-validation is shown in FIG. 6. FIGS. 5 and 6 shows that the minimum PRESS exists between five to seven latent variables.

Figure 7:
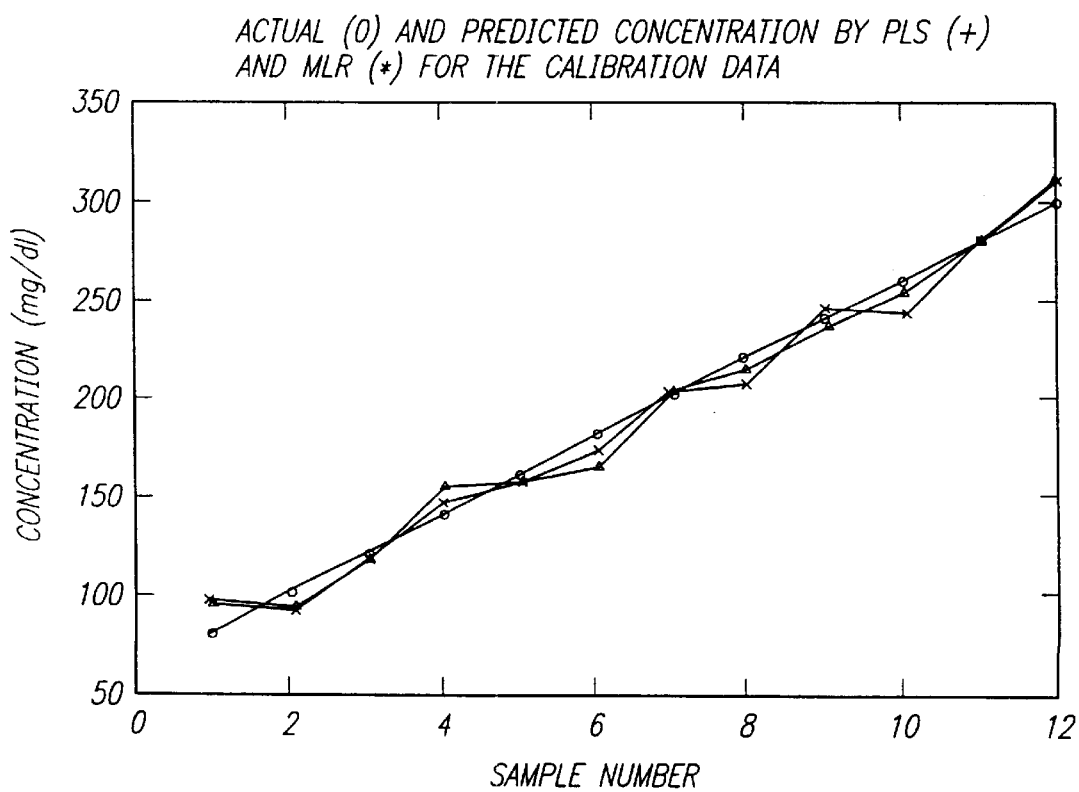
FIG. 7 is a graph of the predicted concentration verses the actual concentration of glucose for the PLS model using six latent variables and for a multiple linear regression (MLR) model derived from the graph of FIG. 2.

The predictive model was tested using samples of known glucose concentration. FIG. 7 shows the results of a prediction test using samples of known glucose concentration in the PLS prediction model using six latent variables, derived from Table I, to define the model. As seen from the graph, the PLS model provides a fairly accurate prediction of the glucose concentration. By way of comparison, the test was repeated for a multiple linear regression (MLR) model based on the same input data. The PLS model generally performs better than the MLR model at lower concentration levels while the MLR model performs better at at higher concentration levels.

Figure 8:
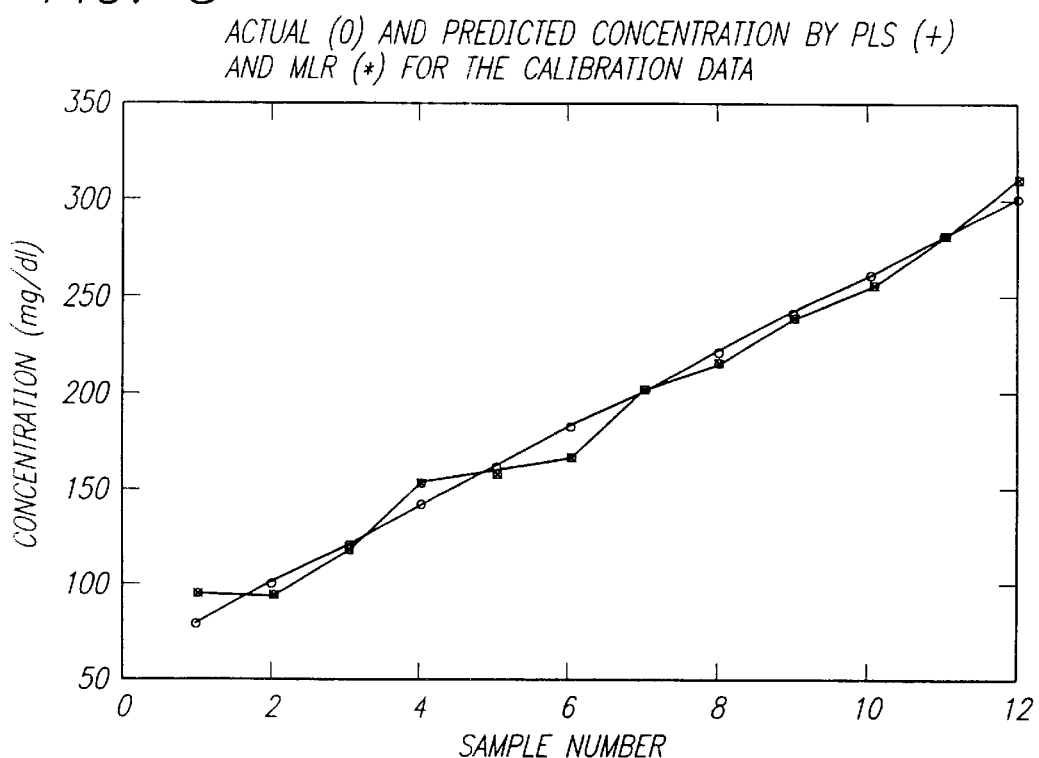
FIG. 8 is a graph of the predicted concentration verses the actual concentration of glucose for the PLS model using seven latent variables and for a multiple linear regression (MLR) model derived from the graph of FIG. 2.

FIG. 8 shows the results of another prediction test again using samples of known glucose concentration in testing PLS and MLR models. However, for this test, the PLS model uses seven latent variables to define the model. As can be seen by the graph, both models provide substantially the same results. Thus, using additional latent variables in the model does not necessarily improve the model's prediction accuracy.

However, it can be shown by the following example that the predictive model can be improved by using a greater number of wavelengths for generating the model. The emissions spectra from the 1,024 elements of the detector array provides a like number of intensity values. Approximately 200 of these points are in the wavelength range of glucose UV-visible emission light (approximately 335 to 450 nanometers) and the data is truncated to this range. To reduce the effects of noise, the spectra is measured three to five times for each glucose concentration. An average of each of these spectra is used to generate the model. To further remove noise, a smoothing function is performed on the spectra using a three point moving average ($X_i$ (smoothed)=$(X_{i-1}+X_i+X_{i+1})/3$. The data for the truncated smoothed spectra was converted into a smaller file by averaging three points at a time to arrive at one point. For example, 180 points become 60 points. Thus, 60 wavelengths for each concentration level, preconditioned as discussed above, are analyzed in this example to arrive at a predictive model using the PLS regression technique, instead of the eight different wavelengths from Table 1 used in the previous example.

Figure 9:
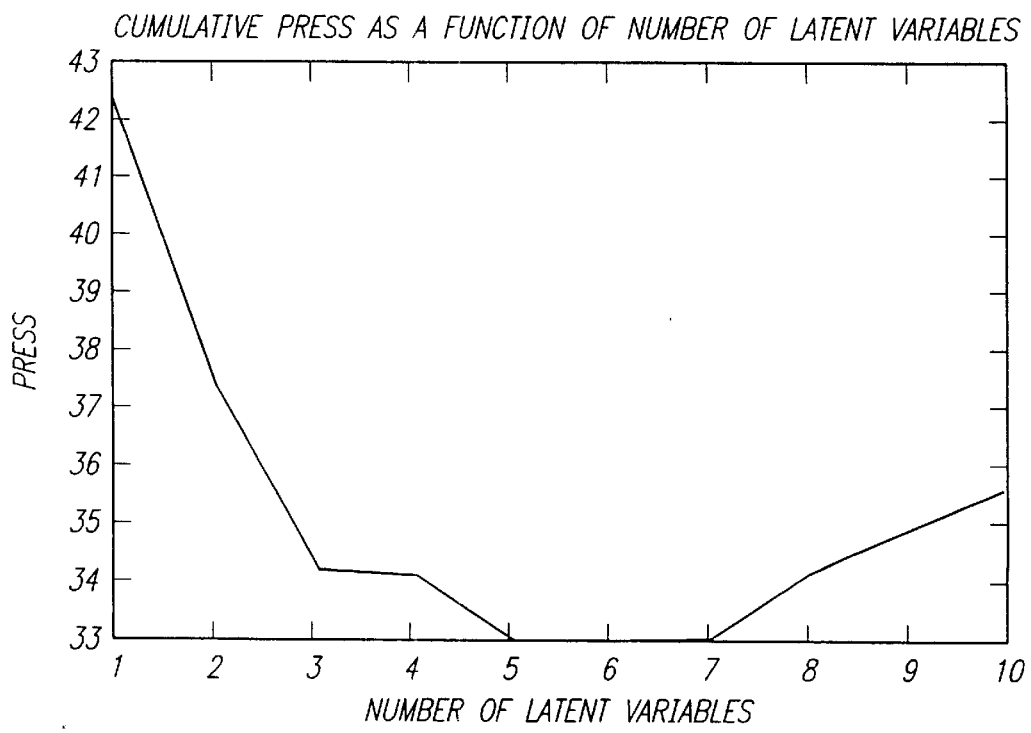
FIG. 9 is a graph of the PRESS versus number of latent variables using one spectra at a time to test a PLS model derived from the whole spectra of the graph of FIG. 2.
Figure 10:
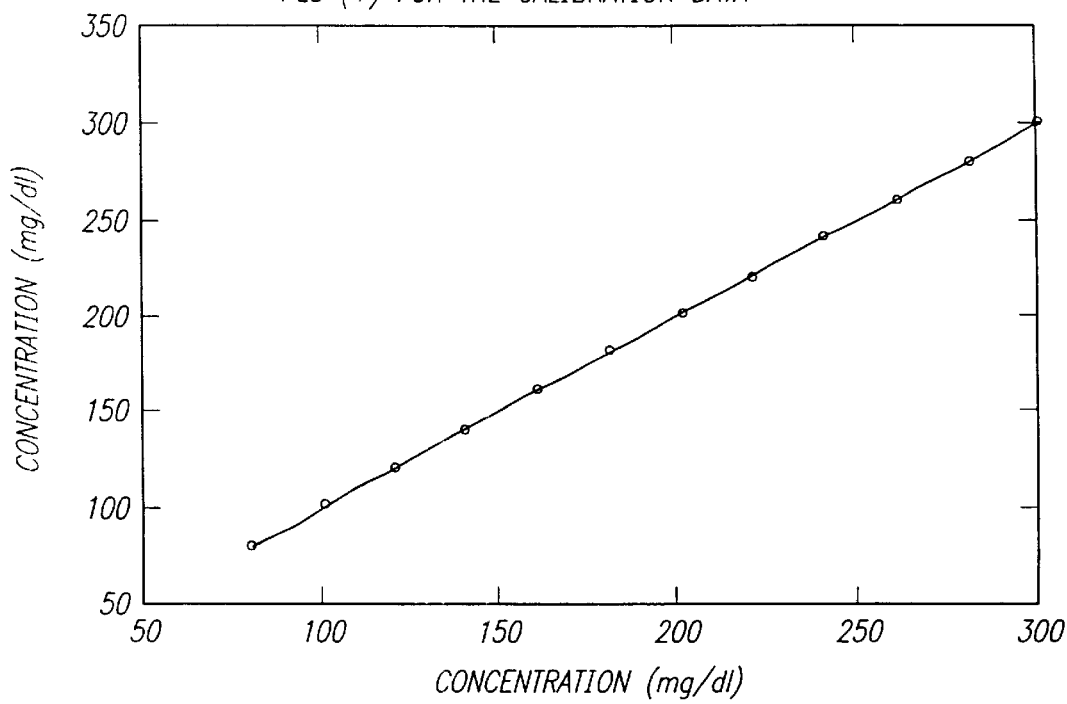
FIG. 10 is a graph of the actual concentration verses the predicted concentration for the PLS model using six latent variables derived from the whole spectrum of the graph of FIG. 2.

As shown in FIG. 9, the PRESS plot for the model using the whole spectra indicates a minimum PRESS at six latent variables. A test of the model using samples of known concentration is shown in FIG. 10. As can be seen by the graph, the PLS predictive model, using the preconditioned spectra, provides a very accurate prediction of the glucose concentration. Given the generally noisy nature of the spectral measurements, and the non-linear relationship between the glucose concentration and the emission intensity at any given wavelength of interest, the results indicated in FIG. 10 are indeed surprising.

Figure 11:
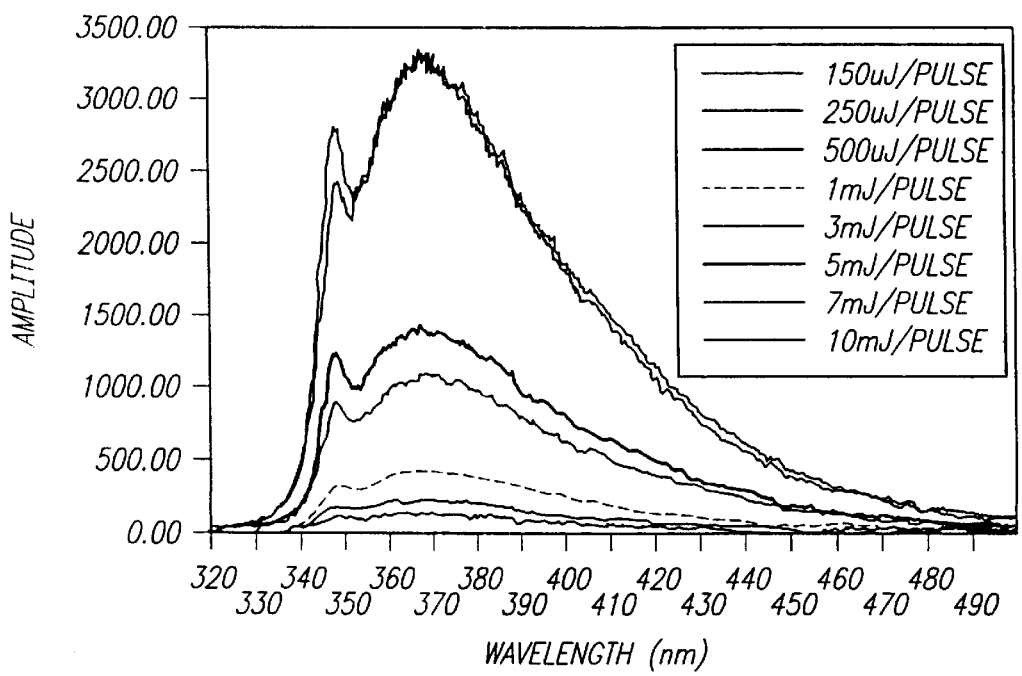
FIG. 11 is a graph of the intensity of glucose emission verses wavelength, at different excitation energy levels, for glucose in water at a concentration of 500 milligrams per deciliter.

A second embodiment of the present invention focuses on the nonlinear relationship between the glucose concentration and the intensity of the excitation light. FIG. 11 shows emission spectra, at a single glucose concentration, resulting from excitation light delivered at different intensity levels. As shown in Table IV below, the emission intensity at a wavelength associated with the raman peak, normalized with respect to the broader florescence peak, is nonlinear with respect to the excitation energy at given concentration level.

TABLE IV

| | Excitation Energy (mj/pulse) | | | | | | |
|---|---|---|---|---|---|---|---|
| Concentr (mg/dl) | .25 | .5 | 1 | 3 | 5 | 7 | 10 |
| 0 | 1 | .92 | .95 | 1 | 1 | 1 | 1 |
| 1 | .78 | .71 | .71 | .76 | .79 | .86 | .84 |
| 10 | .8 | .7 | .73 | .73 | .8 | .84 | .82 |
| 50 | .69 | .64 | .71 | .7 | .77 | .73 | .78 |
| 100 | .74 | .7 | .75 | .81 | .95 | .88 | .87 |
| 500 | .72 | .73 | .67 | .8 | .86 | .72 | .85 |
| 1000 | .84 | .83 | .84 | .84 | .97 | 1 | .93 |

The values in Table IV can be used to provide a predictive model, using the PLS regression technique, as discussed above, with respect to Table I. Thus by varying the intensity or energy of the excitation light, the glucose concentration of an unknown sample can be determined using a predictive model provided by PLS analysis.

Figure 12:
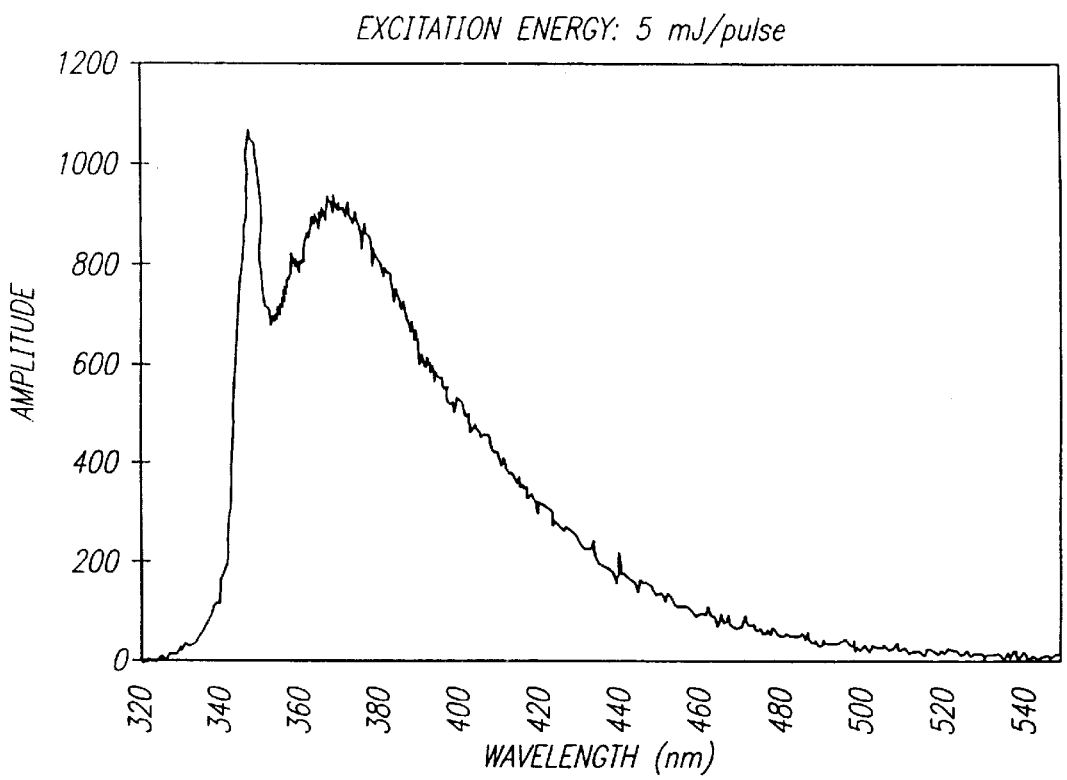
FIG. 12 is a graph of emission intensity versus wavelength for distilled water excited at an excitation energy of 5 millijoules per pulse.

The present invention takes into account the nonlinear nature of the physical interaction between the glucose molecules and the water molecules. FIG. 12 shows the emission spectrum of distilled water illuminated by excitation light having an energy of 5 millijoules per pulse (18 millijoules per millimeter per square millimeter). The graph shows that the florescence spectra for distilled water exhibits a broad florescence band with a peak at approximately 370 nanometers and a narrow raman scattering band at approximately 346 nanometers. The raman scattering band results from scattered incident light having its wavelength shifted by the energy (rotational and translational) of the water molecules.

Figure 13:
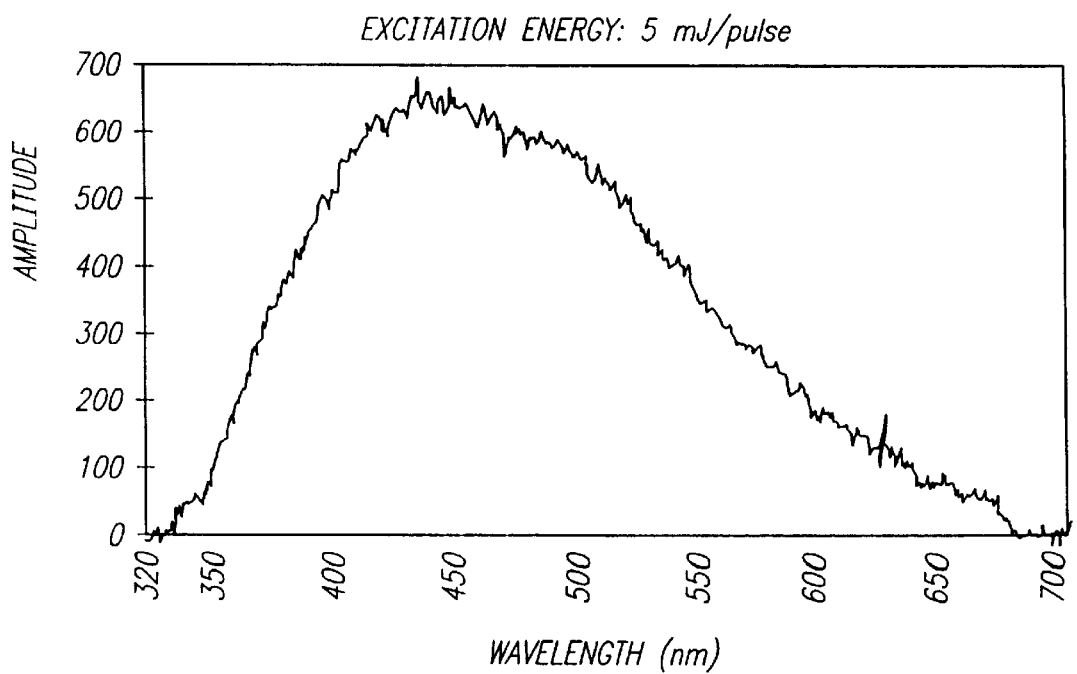
FIG. 13 is a graph of the emission intensity verses wavelength for ultra-anhydrous glucose excited at an excitation energy of 5 millijoules per pulse.
Figure 14:
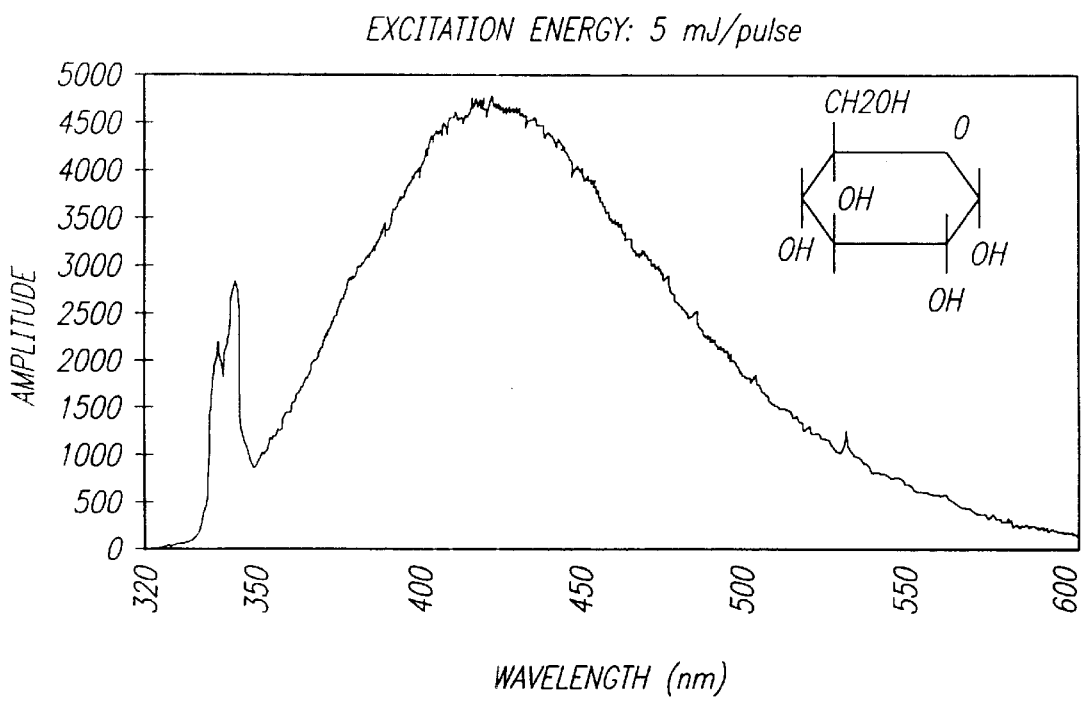
FIG. 14 is a graph of the emission intensity verses wavelength for anhydrous glucose excited at 5 millijoules per pulse.
Figure 15:
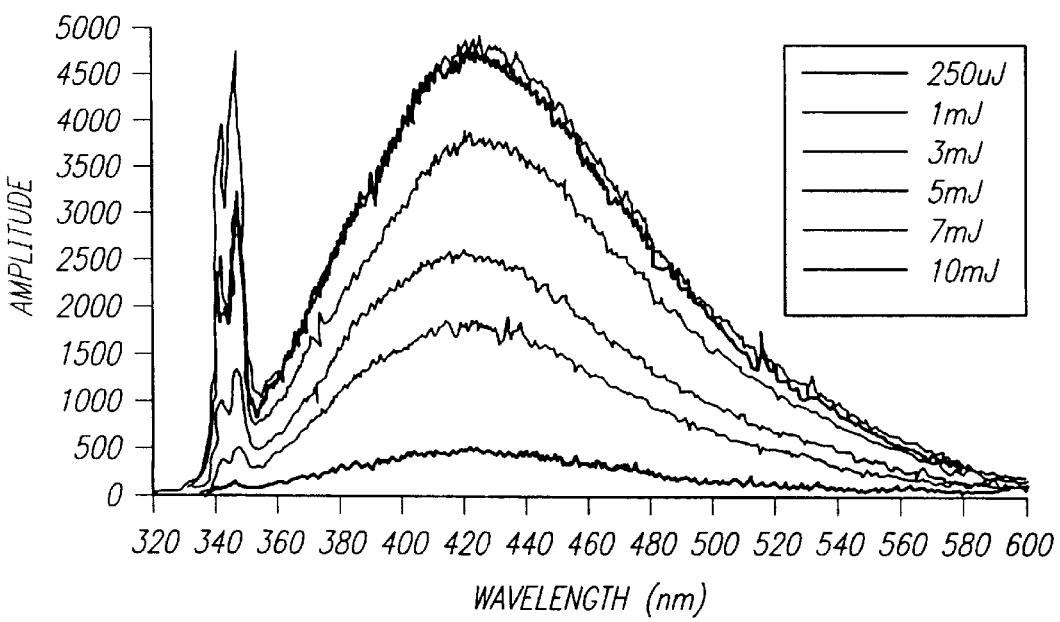
FIG. 15 is a graph of the emission intensity versus wavelength for anhydrous glucose excited with excitation light having an energy at different levels between 0.25 and 10 millijoules per pulse.

The emission spectrum of ultra anhydrous glucose is shown in FIG. 13. The resulting spectrum has a single broad fluorescence band that peaks at approximately 450 nanometers. As shown in FIG. 14, the emission spectrum of anhydrous glucose, which has absorbed a small but spectrally significant amounts of water, exhibits two narrow raman scattering bands that peak at 341 nanometers and 346 nanometers, respectively, and one broad emission band that peaks at about 420 nanometers. The raman scattering peak at 346 nanometers corresponds to the raman peak of water shown in FIG. 12. The raman scattering peak at 341 nanometers apparently results from interaction between the water and glucose molecules. Further, the spectrum of the anhydrous glucose is shifted to shorter wavelengths when compared with the spectrum of the ultra anhydrous glucose shown in FIG. 13. The emissions spectra of anhydrous glucose, as the excitation energy is varied, are shown in FIG. 15. The intensity of spectra generally increase as the excitation energy increases. However, the intensity ratio between the peaks of the raman bands and the broad emission band does not remain constant as the excitation energy increases.

Figure 16:
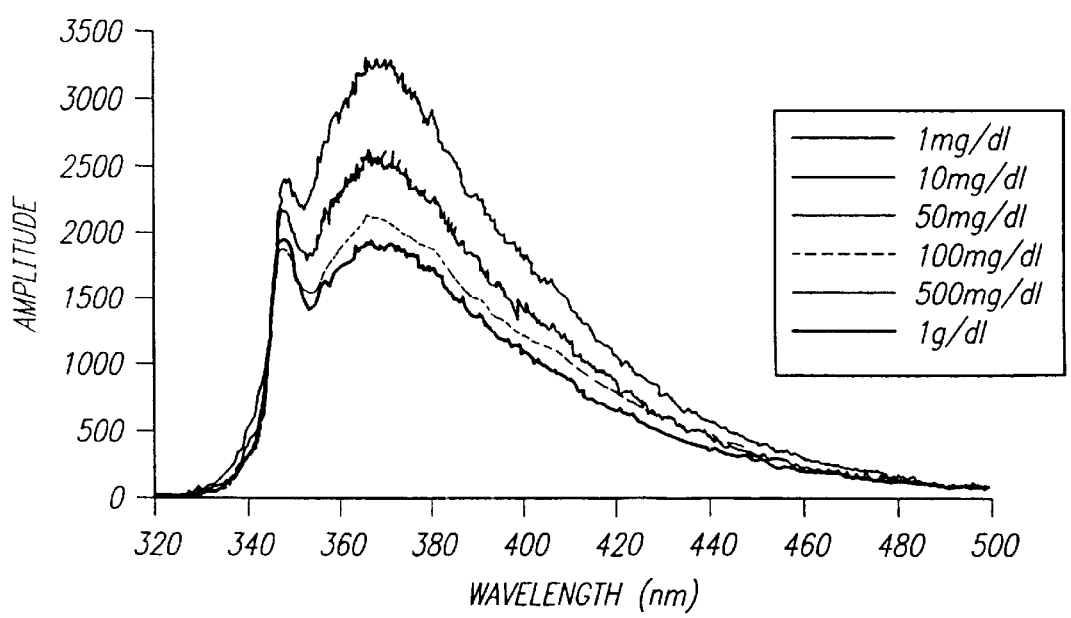
FIG. 16 is a graph of the intensity of glucose emission verses wavelength for different concentrations of glucose in water, illuminated with laser excitation light having a wavelength of 308 nanometers and an excitation energy of 7 millijoules per pulse.

Further, as shown in FIG. 16, the ratio between the raman scattering band and the broad emission band similarly does not remain constant as the concentration increases. Accordingly, the interaction between the water and glucose molecules, and the energy density of the excitation light all appear to effect the resulting emission spectra. Accordingly, simple linear models are effective as an approximation only along very narrow, discrete segments of possible glucose concentrations of interest.

From the foregoing, it will be appreciated that the glucose concentration can be accurately predicted in spite of signal noise and nonlinear relationships between the glucose concentration and certain spectroscopic parameters of interest. The prediction is performed using a model developed from a PLS regression analysis.

Although the foregoing discloses preferred embodiments of the present invention, it is understood that those skilled in the art may make various changes to the preferred embodiments shown without departing from the scope of the invention. The invention is defined only by the following claims.

We claim:

1. Apparatus for determining the concentration of glucose in a sample that includes water, comprising:
   a light source that emits ultraviolet excitation light of at least one predetermined energy level, that is directed at a sample to produce return light from the sample, such return light including induced emission of light produced as a result of interactions between the excitation light and any glucose with water present in the sample;
   a sensor that monitors the return light and generates at least three electrical signals indicative of the intensity of return light associated with glucose concentration distinguishing characteristics of the emission light, the at least three electrical signals including at least two electrical signals indicative of the intensity of return light at a respective number of wavelengths within a predetermined, narrow wavelength band corresponding to at least one characteristic narrow spectral peak, and a third electrical signal indicative of the intensity of return light within a predetermined, narrow wavelength band outside of the narrow spectral peak; and
   a processor that processes the electrical signals, using a predictive model, to determine the concentration of glucose in the sample.

2. Apparatus for determining the concentration of glucose in a sample as recited in claim 1, wherein:
   the predetermined narrow wavelength band ranges from about 330 nanometers to about 360 nanometers.

3. Apparatus for determining the concentration of glucose in a sample as recited in claim 1, wherein the sensor generates a plurality of electrical signals that indicate the intensity of return light substantially continuously across an extended wavelength spectrum associated with the emission light.

4. Apparatus for determining the concentration of glucose in a sample as recited in claim 1, further including one or more waveguides for transmitting the excitation light from the light source to the sample and for transmitting the return light from the sample to the sensor.

5. Apparatus for determining the concentration of glucose in a sample as recited in claim 1, wherein the sensor includes:
   a first detector adapted to detect the return light within a first wavelength band and generate a first electrical signal;
   a second detector adapted to detect the return light within a second wavelength band and generate a second electrical signal; and
   a third detector adapted to detect the return light within a third wavelength band and generate a third electrical signal.

6. Apparatus for determining the concentration of glucose in a sample as recited in claim 3, wherein the predictive model is defined by six latent variables.

7. Apparatus for determining the concentration of glucose in a sample as recited in claim 1, wherein the predictive model is defined by prediction coefficients that are associated with the glucose concentration distinguishing characteristics.

8. Apparatus for determining the concentration of glucose in a sample as defined in claim 1, wherein:
   the energy of the excitation light is varied over a plurality of predetermined energy levels; and
   the sensor generates, at each energy level, a first electrical signal based on the intensity of return light within a wavelength of the emission light associated with raman scattering, and a second electrical signal based on the intensity of return light within a wavelength band of the emission light associated with a peak of a broad glucose emission band.

9. An apparatus for determining the concentration of glucose in a sample that includes water, comprising:
   a light source that emits ultraviolet excitation light that is varied over a plurality of predetermined energy levels and directed at a sample to produce return light from the sample, such that the return light includes induced emissions of light produced as a result of interactions between the excitation light and any glucose with water present in the sample;
   a sensor that monitors the return light and generates, at each energy level of the excitation light, an electrical signal indicative of a first intensity of return light within a wavelength of the return light associated with raman scattering, and an electrical signal indicative of a second intensity of return light within a wavelength of the return light associated with glucose emission; and
   a processor that processes the electrical signals, using a predictive model, to determine the concentration of glucose in the sample.

10. A method for determining the concentration of glucose in a sample including water, comprising:
    exciting the sample with excitation light at a plurality of energy levels;
    measuring, at each energy level, a first intensity of return light within a wavelength of the return light associated with raman scattering;
    measuring, at each energy level, a second intensity of return light within a wavelength of the return light associated with glucose emission;

determining the concentration of glucose using a predictive model incorporating the first intensity measurements and the second intensity measurements.

11. Apparatus for determining the concentration of glucose in a sample that includes water, comprising:

a light source that emits ultraviolet excitation light of at least one predetermined energy level, that is directed at a sample to produce return light from the sample, such return light including induced emissions of light produced as a result of interactions between the excitation light and any glucose with water present in the sample;

a sensor that monitors the return light within eight different wavelength bands and generates eight electrical signals indicative of the intensity of return light within respective wavelength bands, and which are associated with glucose concentration distinguishing characteristics of the emission light; and a processor that processes the electrical signals, using a predictive model, to determine the concentration of glucose in the sample.

12. Apparatus for determining the concentration of glucose in a sample as recited in claim 11, wherein:

the wavelength of the excitation light is about 308 nanometers;

the first wavelength band is a narrow wavelength band centered at about 342 nanometers;

the second wavelength band is a narrow wavelength band centered at about 344 nanometers;

the third wavelength band is a narrow wavelength band centered at about 347 nanometers;

the fourth wavelength band is a narrow wavelength band centered at about 352 nanometers;

the fifth wavelength band is a narrow wavelength band centered at about 360 nanometers;

the sixth wavelength band is a narrow wavelength band centered at about 370 nanometers;

the seventh wavelength band is a narrow wavelength band centered at about 385 nanometers; and the eighth wavelength band is a narrow wavelength band centered at about 400 nanometers.

13. A method of determining the concentration of glucose in a sample with water, comprising:

providing a regression model that accounts for a nonlinear relationship between the concentration of glucose in a sample and an electrical signal based on certain glucose concentration distinguishing characteristics of a light emission spectrum that includes emission light produced by glucose related interactions with the excitation light;

causing a sample to produce a light emission spectrum that includes ultraviolet emission light produced by glucose related interaction and generating a plurality of electrical signals that represent the glucose concentration distinguishing characteristics, at least two of the plurality of electrical signals indicative of the intensity of return light at a respective number of wavelengths within a predetermined, narrow, wavelength band corresponding to at least one characteristic narrow spectral peak, and at least a third of the plurality of electrical signals indicative of the intensity of return light within a predetermined, narrow wavelength band outside of the narrow spectral peak; and processing, using the regression model, the plurality of electrical signals to determine the glucose concentration and generating an electrical signal based on the glucose concentration determined using the regression model.

* * * * *